(12) United States Patent
Farri et al.

(10) Patent No.: US 11,275,905 B2
(45) Date of Patent: Mar. 15, 2022

(54) SYSTEMS AND METHODS FOR SEMANTIC SEARCH AND EXTRACTION OF RELATED CONCEPTS FROM CLINICAL DOCUMENTS

(71) Applicant: KONINKLIJKE PHILIPS N.V., Eindhoven (NL)

(72) Inventors: Oladimeji Feyisetan Farri, Yorktown Heights, NY (US); Xianshu Zhu, Ossining, NY (US); Junyi Liu, Revere, MA (US)

(73) Assignee: Koninklijke Philips N.V., Eindhoven (NL)

( * ) Notice: Subject to any disclaimer, the term of this patent is extended or adjusted under 35 U.S.C. 154(b) by 805 days.

(21) Appl. No.: 15/551,627

(22) PCT Filed: Mar. 8, 2016

(86) PCT No.: PCT/IB2016/051291
§ 371 (c)(1),
(2) Date: Aug. 17, 2017

(87) PCT Pub. No.: WO2016/142846
PCT Pub. Date: Sep. 15, 2016

(65) Prior Publication Data
US 2018/0068076 A1    Mar. 8, 2018

Related U.S. Application Data

(60) Provisional application No. 62/130,141, filed on Mar. 9, 2015.

(51) Int. Cl.
*G06F 40/45* (2020.01)
*G06F 16/903* (2019.01)
(Continued)

(52) U.S. Cl.
CPC ........ *G06F 40/45* (2020.01); *G06F 16/90344* (2019.01); *G06F 40/232* (2020.01);
(Continued)

(58) Field of Classification Search
CPC combination set(s) only.
See application file for complete search history.

(56) References Cited

U.S. PATENT DOCUMENTS 9,665,662 B1 *   5/2017   Gautam et al.
2004/0044548 A1 * 3/2004   Marshall et al.
(Continued)

*Primary Examiner* — Michael Tomaszewski
*Assistant Examiner* — William T. Monticello

(57) ABSTRACT

When performing semantic search for related clinical concepts based on their semantic meaning, a semantic search engine framework employs a client web interface (12) (e.g., a browser) that receives keyword search information (14), and a web server (16) that communicates with a semantic analysis engine (18). A natural language processing (NLP) engine (server) (22) receives and stores clinical notes and information (24), extracts clinical concepts from the clinical notes and stores them in a NoSQL database (26). The NLP engine converts unstructured free text notes into structured actionable data. The semantic analysis engine analyses user-entered keywords, maps them to a UMLS concept, and identifies related concepts based on one or more relational knowledge sources. The web server searches for the related concept IDs in the NoSQL database and returns a list (28) of relevant notes and concepts for display to, and selection by, the user.

19 Claims, 12 Drawing Sheets

(51) Int. Cl.
    *G06F 40/232* (2020.01)
    *G16H 70/60* (2018.01)
    *G16H 10/60* (2018.01)
    *G16H 10/20* (2018.01)

(52) U.S. Cl.
    CPC ............ *G16H 10/20* (2018.01); *G16H 10/60* (2018.01); *G16H 70/60* (2018.01)

(56) References Cited

U.S. PATENT DOCUMENTS

2007/0143273 A1* 6/2007 Knaus et al.
2008/0208631 A1* 8/2008 Morita et al.
2011/0004628 A1* 1/2011 Armstrong et al.
2011/0047169 A1* 2/2011 Leighton et al.
2014/0330586 A1* 11/2014 Riskin et al.
2015/0149461 A1* 5/2015 Aguilar Lemarroy et al.
2015/0370979 A1* 12/2015 Boloor et al.
2015/0379241 A1* 12/2015 Furst et al.
2016/0019299 A1* 1/2016 Boloor et al.
2016/0019356 A1* 1/2016 Martin et al.
2016/0048655 A1* 2/2016 Maitra et al.
2016/0120433 A1* 5/2016 Hughes
2016/0132572 A1* 5/2016 Chang et al.
2017/0061102 A1* 3/2017 Weber et al.

* cited by examiner

- Acute coronary syndrome [Context 1]
  - SNOMED CT Concept
    - Clinical finding
      - Finding by site
        - Disorder by body site
          - Disorder of trunk
            - Disorder of thorax
              - Disorder of mediastinum
                - Heart disease
                  - Acute heart disease
                    - Acute ischemic heart disease

FIG. 7

SYSTEMS AND METHODS FOR SEMANTIC SEARCH AND EXTRACTION OF RELATED CONCEPTS FROM CLINICAL DOCUMENTS

CROSS-REFERENCE TO PRIOR APPLICATIONS

This application is the U.S. National Phase application under 35 U.S.C. §371 of International Application No. PCT/M2016/051291, filed on Mar. 8, 2016, which claims the benefit of U.S. Provisional Application No. 62/130,141, filed on Mar. 9, 2015. These applications are hereby incorporated by reference herein.

The present invention finds application in patient healthcare data systems and methods. However, it will be appreciated that the described techniques may also find application in other document management systems, other data management techniques, and the like As more and more patient health records become digitalized, much work has been done on clinical concepts extraction which maps clinical notes to unified medical terminologies such as UMLS, SNOMED-CT. Such work turns unstructured free-text clinical notes into structured, codified format which is more suitable for further information retrieval, including search functionalities. Current clinical search engines are mostly based on simple keyword matching.

In the last few decades, clinical research interests within academia and industry have increasingly focused on the extraction of vital patient details e.g. findings and problems from clinical documents towards improving the quality of patient care. These clinical documents largely comprise free text (narratives) that provide significant information over and above structured alternatives such as laboratory data and vital signs. However, these documents often highlight the patient's healthcare utilization over an extensive period and contain large quantities of information that can overwhelm the cognitive capacity of healthcare providers reading and using the documents. Notable projects employing various NLP techniques for information extraction from clinical documents include the Medical Language Extraction and Encoding System (MEDLEE) and MetaMap, which have been used to map concepts within clinical and biomedical text to the unified medical language system (UMLS). In addition, shared tasks and challenges such as the informatics for integrating biology and the bedside (i2b2) challenge promote various NLP tasks related to clinical concept extraction by providing access to otherwise expensive annotated corpora for the clinical domain. Despite several peer-reviewed literature on modules for clinical NLP targeted at both codifying entire clinical documents and retrieving specific patient information e.g. detecting acute respiratory infections, projects focused on applying NLP technology towards optimizing the use of clinical documents within telehealth-related workflows have not been rigorously explored. A related work in the telehealth space proposes a virtual network that uses NLP for retrieving signs and symptoms towards clinical decision support for patient queries within the Pakistani healthcare system. However, this virtual network does not focus on workflow optimization relevant to the consumption of free text clinical documents by clinicians (specifically Nurses and Physicians).

Traditional workflow optimization approaches involve clinicians manually retrieving active (unresolved) diagnoses from clinical documents within electronic health record (EHR) systems (e.g. EPIC, Cerner, etc.). The information overload and cognitive burden associated with manual retrieval of active diagnoses often complicates the clinicians' workflow, with the resulting complexity leading to suboptimal information synthesis, increased healthcare cost from re-ordering investigations to evaluate diagnoses that may have been previously documented, and an increased risk of errors in clinical care due to unretrieved albeit available patient data.

Despite the maturity of semantic search technologies (e.g. comprehensive domain-based ontologies, information extraction methodologies, and reasoning engines) over the last few years, the clinical informatics industry has yet to produce a well-recognized information retrieval application providing semantic search functionalities to support routine healthcare tasks and clinical research. Knowledge resources with significant coverage of the clinical domain e.g. the Unified Medical Language System (UMLS) have been used to reduce the complexity of the clinical concepts and categorize these concepts based on semantic types. However, much work still needs to be done to effectively utilize the relationships embedded in such knowledge sources towards facilitating navigational and research-oriented review of context-ware patient information.

In the radiology domain, the speech recognition and dictation software called Nuance PowerScribe 360® provides a Montage™ plug-in which enables search-driven analysis of patient information to support quality evaluation. However, this plug-in does not offer much needed context-aware, semantically related search results useful for navigational and research-oriented review of large amounts of free text patient reports, both within and beyond the radiology domain.

The present application provides new and improved systems and methods that facilitate automatically extracting active diagnoses from electronic clinical documents, thereby overcoming the above-referenced problems and others.

In accordance with one aspect, a system that facilitates using user-entered keywords to search for related clinical concepts based on the sematic meaning of the keywords comprises a client web interface that receives keyword search information, and a semantic analysis engine that receives the keyword search information via a web server and communicates with a natural language processing (NLP) engine via a MySQL™ database. The NLP engine receives and stores clinical notes and information and extracts clinical concepts from the clinical notes and stores them into a NoSQL database. The semantic analysis engine analyses the keyword search information, maps keywords to at least one UMLS concept, identifies and retrieves one or more related concepts based on one or more relational knowledge sources. The web server searches for the related concepts in the NoSQL database and returns a list of relevant notes and concepts to the web server for display to a user via the client web interface.

According to another aspect, a method of automated extraction of active diagnoses from electronic clinical documents comprises receiving a free-text electronic document generated during patient care, identifying document sections with active diagnoses, identifying at least one noun-phrase (NP) terminal within the identified sections, and generating a set of dual keys from each NP terminal. The method further comprises querying a database using the dual keys, identifying candidate active diagnoses based on the concatenated characters, selecting a candidate active diagnosis that is most-similar to the NP terminal based on syntactic, semantic, and hierarchical features, and presenting a list of active diagnoses extracted from the free-text document. Additionally, the method comprises analyzing a hierarchical tree that represents relationships associated with words within each candidate active diagnosis as compared to that of words within a concept identified within the NP terminal to evaluate a semantic relatedness between the given active diagnosis and the NP terminal concept.

According to another aspect, a graphical user interface that facilitates presenting clinical concepts related to user-entered keywords based on the semantic meaning of the keywords comprises a keyword field via which a user enters or selects one or more keywords, a results panel that displays a list of highlighted annotated clinical concepts that are semantically related to the one or more keywords, and an ontology panel that displays an ontology-derived tree for a user-selected clinical concept. The graphical user interface further comprises one or more expandable and collapsible report sections that, when expanded, provide a selectable link to the user to a full clinical report associated with the user-selected clinical concept.

Still further advantages of the subject innovation will be appreciated by those of ordinary skill in the art upon reading and understand the following detailed description.

The patent or application file contains at least one drawing executed in color. Copies of this patent or patent application publication with color drawings will be provided by the Office upon request and payment of the necessary fee.

The drawings are only for purposes of illustrating various aspects and are not to be construed as limiting.

FIG. 7 shows a SNOMED CT tree for acute coronary syndrome such as is displayed to a clinician, in accordance with one or more features described herein.

Figure 1:
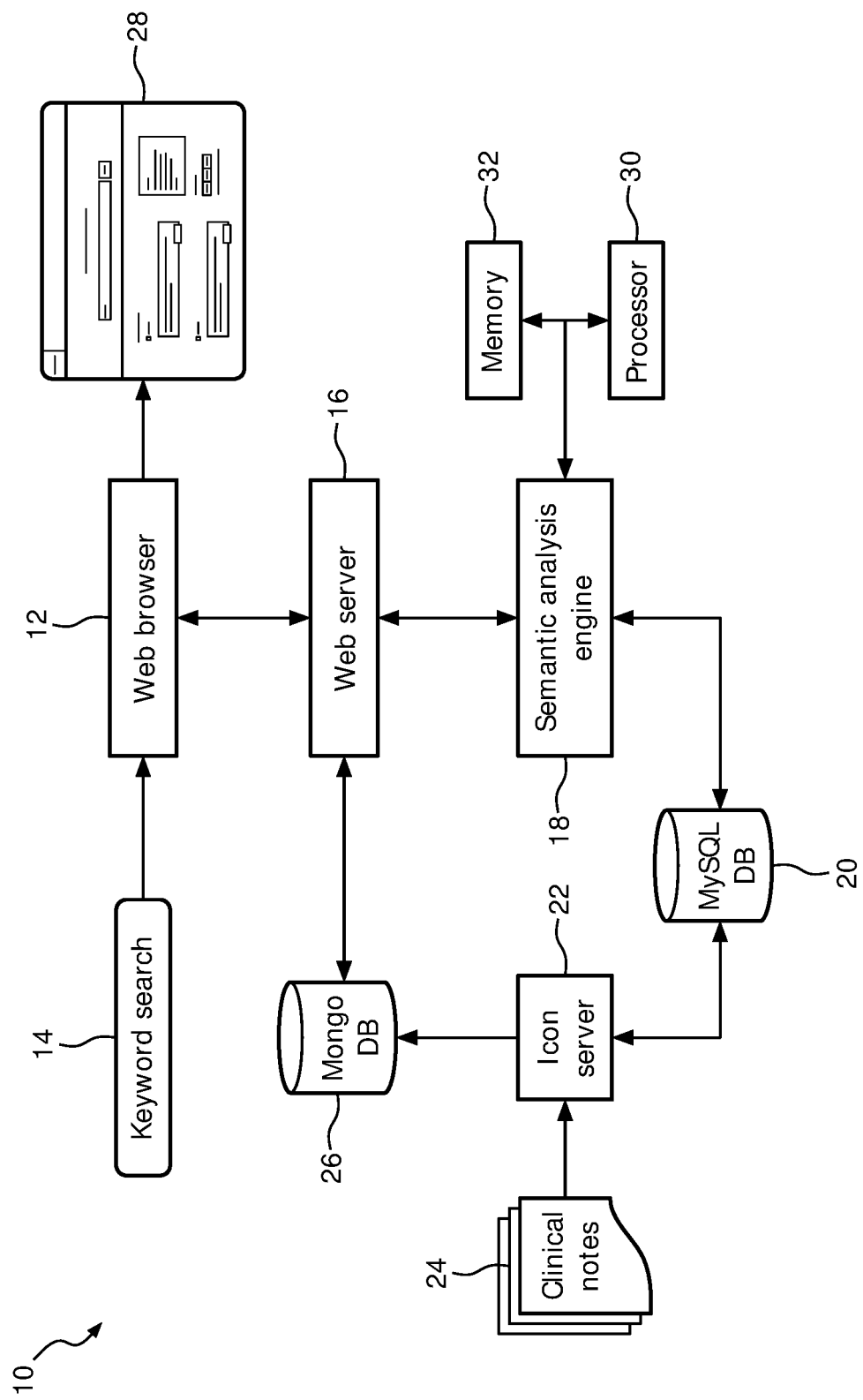
FIG. 1 illustrates a semantic search framework or system that permits users (e.g., clinicians) to search for related clinical concepts based on their semantic meaning, in accordance with one or more aspects described herein.

The described systems and methods overcome the above-mentioned problems by extending the functionality of traditional search engine by providing search results that are relevant in semantic meaning as compared to simple keyword matching. The use of a semantic search system in the clinical domain facilitates providing patient care in a more informed and efficient way. The herein-described semantic analysis engine in the search framework enables physicians to find relevant diagnoses which are not obvious at first glance. With the use of NoSQL database (e.g., MongoDB™) in the system, large scale population-based analysis is enabled. The described systems and methods support systematic synthesis of patient information by healthcare providers, administrators and researchers to permit effective individual-patient and population-based analyses of healthcare utilization and quality.

The semantic search system facilitates automatically correcting user-entered keywords into the most appropriate clinical concepts, while effectively analyzing and identifying semantically-relevant concepts based on specific medical terminologies (e.g., UMLS, SNOMED-CT, Radlex®, FMA, etc.). Automated mapping between Radlex® and SNOMED terms using FMA (Foundational Model of Anatomy ontology) is also provided. Moreover, the system is scalable: in one embodiment, the system is built using, e.g., a Django framework and is scalable with the use of MongoDB™.

Effective information synthesis from clinical documents generated during patient care depends on complex cognitive processes performed by multi-tasking healthcare providers. Clinical documents largely comprise free text (narrative) entries that provide significant information over and above structured alternatives such as laboratory data and vital signs. However, these documents often highlight the patient's healthcare utilization over an extensive period and contain large quantities of information that can overwhelm the cognitive capacity of healthcare providers reading and using the documents. For instance, when using the Philips IntelliSpace eCareManager (eCM), a commercial telehealth platform used in monitoring critically-ill patients, nurses and physicians need to document active (unresolved) diagnoses following their review of patients' clinical documents retrieved from various electronic health record (EHR) systems such as EPIC, Cerner, etc. The information overload and cognitive burden associated with manually retrieving active diagnoses often complicates the clinical care workflow. This workflow complexity in turn can lead to inaccurate information synthesis, increased cost due to re-ordering investigations to evaluate for previously documented diagnoses that are undetected within the documents by the clinicians, and, ultimately, non-trivial errors in patient management. Accordingly, the described systems and methods provide an application that automatically extracts the active diagnoses from clinical documents integrated with the eCM application using natural language processing (NLP) techniques, thereby optimizing the overall clinical care workflow and minimizing the likelihood of errors in information synthesis during critical patient care. In this manner, clinicians are better equipped to improve their workflow efficiency with respect to reviewing clinical documents to identify active diagnoses, minimize risk for errors in retrieving and documenting active diagnoses, and improve access to accurate diagnostic information for better patient care.

The implementation of the described semantic search systems aims at providing more contextually relevant results from large quantities of domain-specific literature over and above the output of simplistic syntax-based, string-matching search functionalities. The use of semantic search systems within the clinical domain facilitates improved synthesis of context-aware patient information necessary for patient care. As a front-end to the Philips home-grown clinical semantic search platform (ICON Semantic Search Engine), a user-centered web-based interface is provided to support efficient navigational and research-based review of semantic search results. The user interface supports systematic synthesis of patient information by healthcare providers, administrators and researchers towards effective individual-patient and population-based analyses of healthcare utilization and quality.

Given the current scarceness of information retrieval applications providing semantic search functionalities to support routine healthcare tasks and clinical research, the described web-based interface tool allows clinician users to efficiently and accurately retrieve semantically-related concepts which may result in evidence of clinical associations exhibited within the patient population which were previously undiscovered. The interface also facilitates easily identifying clinical manifestations that can inform patient sample selection for research and clinical trials, as well as effective navigating to sections and sub-sections within free text reports which contain contextual information relevant to their search interests.

FIG. 1 illustrates a semantic search framework or system 10 that permits users (e.g., clinicians) to search for related clinical concepts based on their semantic meaning, in accordance with one or more aspects described herein. The ICON semantic search engine framework comprises a client web interface 12 (e.g., a browser) that receives keyword search information 14 and is coupled to a web server 16 that provides connectivity and/or communication with a semantic analysis engine 18. The semantic analysis engine communicates with a MySQL™ database 20 that in turn communicates with an ICON natural language processing (NLP) engine (server) 22 that receives and stores clinical notes and information 24. The ICON NLP engine 22 also communicates with a NoSQL database (MongoDB™) 26, which is also in communication with the web server 16.

The ICON NLP engine 22 extracts clinical concepts from the clinical notes 24 and stores them into the NoSQL database 26. Clinical concepts extracted by the ICON NLP engine can include, without limitation, diagnoses, findings, procedures, etc. The ICON engine converts unstructured free text notes into structured actionable data. The structured data becomes the units of analysis for further processing by the semantic analysis engine 18.

The database component of the framework 10 comprises two types of databases: the MySQL™ database 20 and NoSQL database 26. The MySQL™ database serves as a knowledge source for the analysis engine and the ICON engine to support mapping and relationship extraction. The NoSQL database is used to store output from ICON engine, which is structured information that is extracted from the clinical notes. The NoSQL database (MongoDB™) is used as the database engine. NoSQL databases address the shortcomings of traditional relational databases and are widely used in 'Big Data' and real-time web applications. They ensure optimal scalability of the system.

The web interface 12 provides a user-friendly search engine-like interface that allows users to search clinical notes by entering keywords 14. Relevant notes with key concepts highlighted are listed as search results. Users are able to click each concept to view a tree structure of the concept within different ontologies. Users are also able to click and view the original notes for further investigation.

The Web server 16 handles front end user queries, such as a keyword search, shows original notes, shows tree structure for the concepts, etc.

The semantic analysis engine 18 analyses user-entered keywords and maps them to a UMLS concept. Then, related concepts are identified and retrieved based on one or more relational knowledge sources. The search engine 10 searches for the related concept IDs in the NoSQL database 26 and returns a list 28 of relevant notes and concepts. Thus, rather than simply matching keywords, the search engine 10 actually analyses the keywords and understands the underlying semantic meaning of the keywords. The search results are based on the semantic meaning of the keywords.

The system further includes a processor 30 that executes the described modules (e.g., computer-executable instructions, routines, applications, programs, etc.), and a memory 32 on which the modules are stored for execution by the processor. It will be understood that the processor 30 executes, and the memory 32 stores, computer executable instructions for carrying out the various functions and/or methods described herein. The memory 32 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 30 can read and execute. In this context, the described systems may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphics processing unit (GPU), or PAL, or the like.

Figure 2:
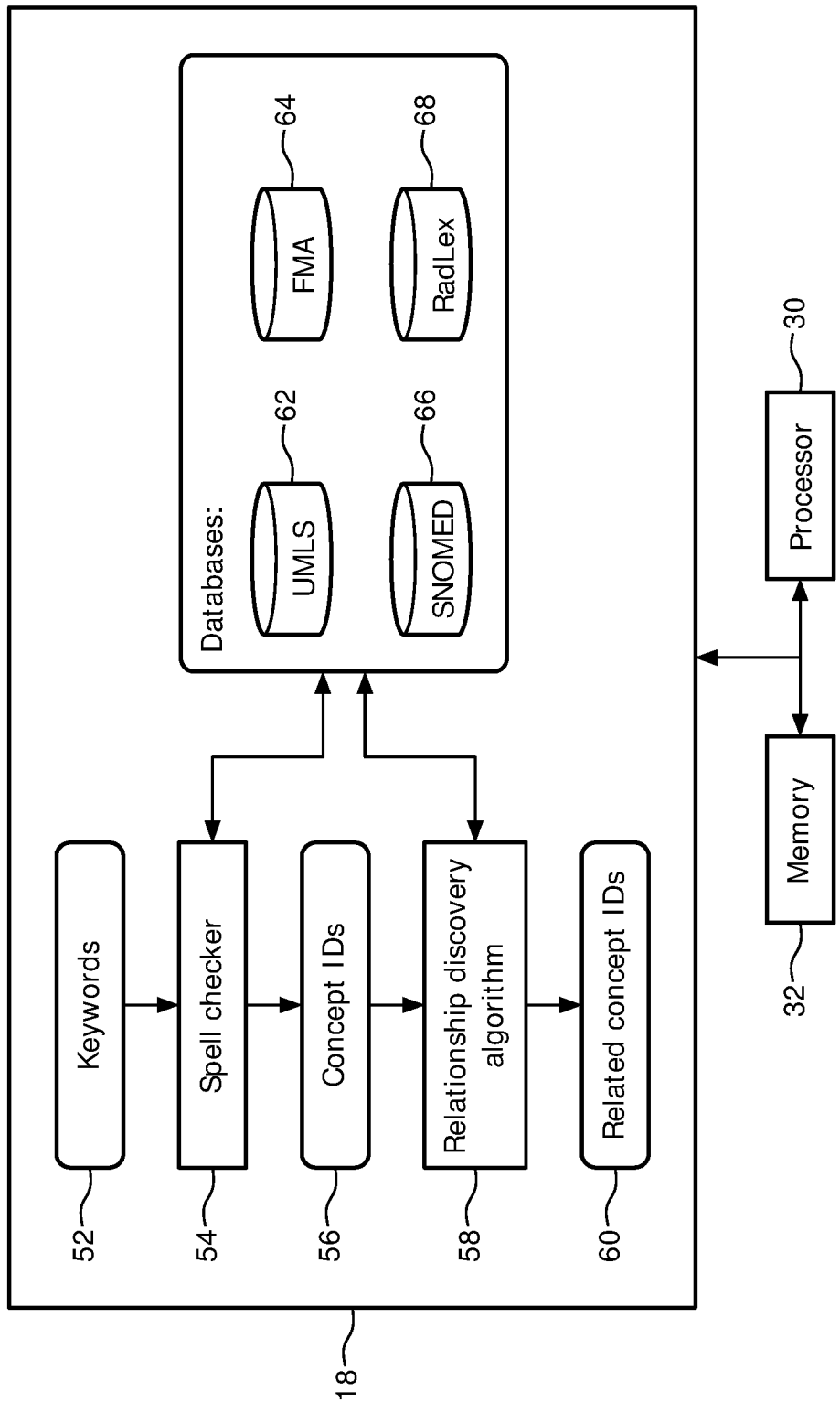
FIG. 2 is an illustration of the semantic analysis engine, in accordance with one or more aspects described herein.

FIG. 2 is an illustration of the semantic analysis engine 18, in accordance with one or more aspects described herein. According to one embodiment, a user initiates a keyword search query. The query is received by the web server 16 (FIG. 1) and relayed to analysis engine 18. The analysis engine analyzes the keywords and returns a set of relevant concept IDs back to the web server 16. The analysis performed by the semantic analysis engine comprises mapping the keywords to a clinical concept and identifying a set of relevant concepts. Once the web server receives the concept IDs returned from the analysis engine, the web server uses the IDs to query the NoSQL database and find relevant clinical notes that include the identified concepts. The final results are displayed on the web browser. In one embodiment, the results are listed chronologically.

As shown in FIG. 2, user-entered keywords 52 are fed into the analysis engine 18. A spell checker module 54 corrects possible spelling errors and maps the keywords to one or more clinical concept IDs 56 using, e.g., a fuzzy string matching algorithm. A relationship discovery algorithm 58 is used to identify related concept IDs 60 to the concept that the user wants to search for. Both the spell checker and relationship discovery algorithm can be constructed based on knowledge sources, including UMLS 62, FMA 64, SNOMED 66, RadLex® 68, etc.

The spell check module 54 is configured to map user-entered keywords to closest matching clinical concepts from a dictionary when there are some spelling errors or word order variants. The dictionary that supports the spell checker is a combination of both a general English (or any other language) dictionary and a medical dictionary. The medical dictionary contains all the medical terms from UMLS, SNOMED, FMA, RadLex®, ICD10 (International Statistical Classification of Diseases and Related Health Problems, version 10), etc.

Figure 3:
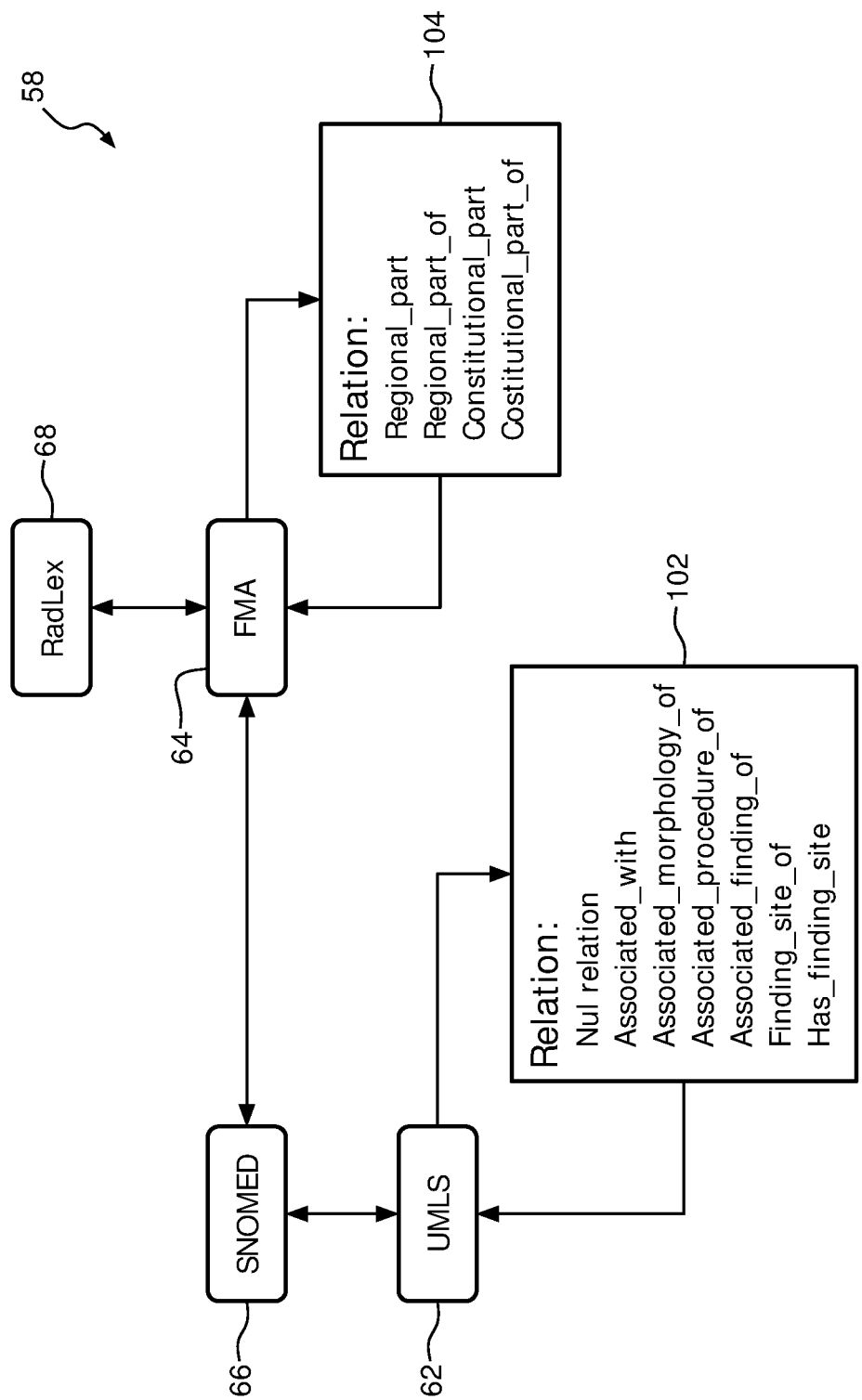
FIG. 3 shows an example of the relationship discovery algorithm flow, in accordance with one or more features described herein.

FIG. 3 shows an example of the relationship discovery algorithm flow 58, in accordance with one or more features described herein. A UMLS 62 (Unified Medical Language System) integrates major terminologies into a single framework for knowledge representation and includes a concept repository and a semantic network. The semantic network comprises a set of useful and important relationships or semantic relations 102 that exist between concepts, such as Null relation, Associated_with, Associated_morphology_of, Associated_procedure_of, Associated_finding_of, Finding_site_of, Has_finding_site, etc. The goal of sematic search is to find diagnoses, findings, or procedures that map to the relevant anatomical structure. One way of achieving this goal is to query the UMLS relation table, and concepts that associate with the above relationships are the relevant concepts. As shown in FIG. 3, an alternative way to find relevant concepts is to map concepts to FMA 64 and expand the FMA candidates by looking at regional and constitutional relations 104, then map FMA 64 back to SNOMED 66 and RadLex® 68 concepts. For SNOMED and FMA mapping, a finding_site attribute is identified for SNOMED concepts from the SNOMED relation table, and then a finding_site is identified for FMA mapping from the UMLS concept table.

Figure 4:
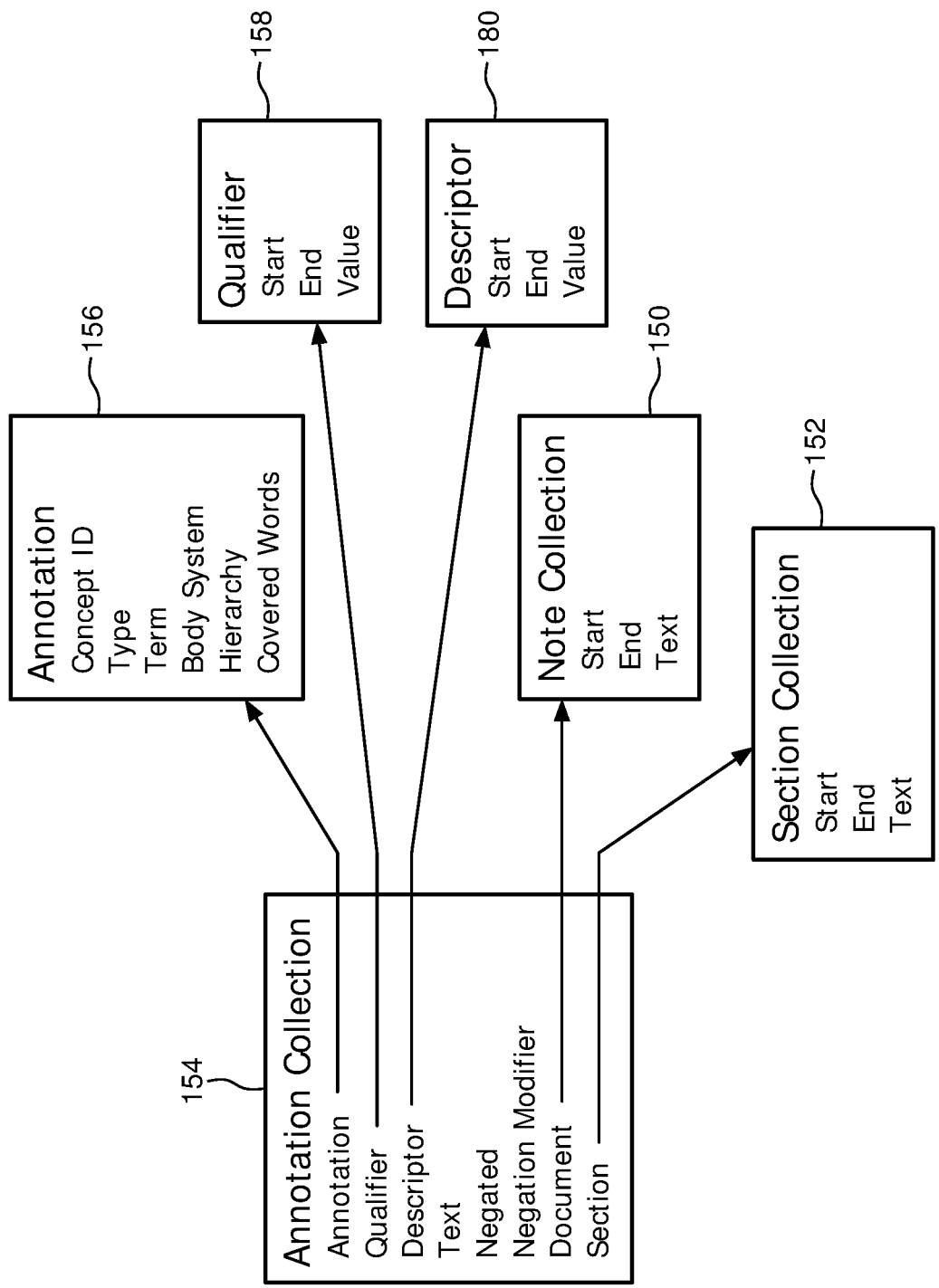
FIG. 4 shows a NoSQL database diagram, in accordance with one or more features described herein.

FIG. 4 shows a NoSQL database diagram, in accordance with one or more features described herein. The output of ICON engine 22 (FIG. 1) is stored in the NoSQL database 26 (FIG. 1) (e.g., MongoDB™). Information is stored into three different collections, as shown in FIG. 4: a notes collection 150, a section collection 152, and an annotation collection 154. This structure is designed to facilitate fast searching and retrieving. The annotation collection 154 comprises a plurality of annotations 156, (e.g., concept IDs, annotation type, etc.), as well as qualifier information 158 (e.g., start, end, value, etc.) and descriptor information 160 (e.g., start, end, value, etc.).

Figure 5:
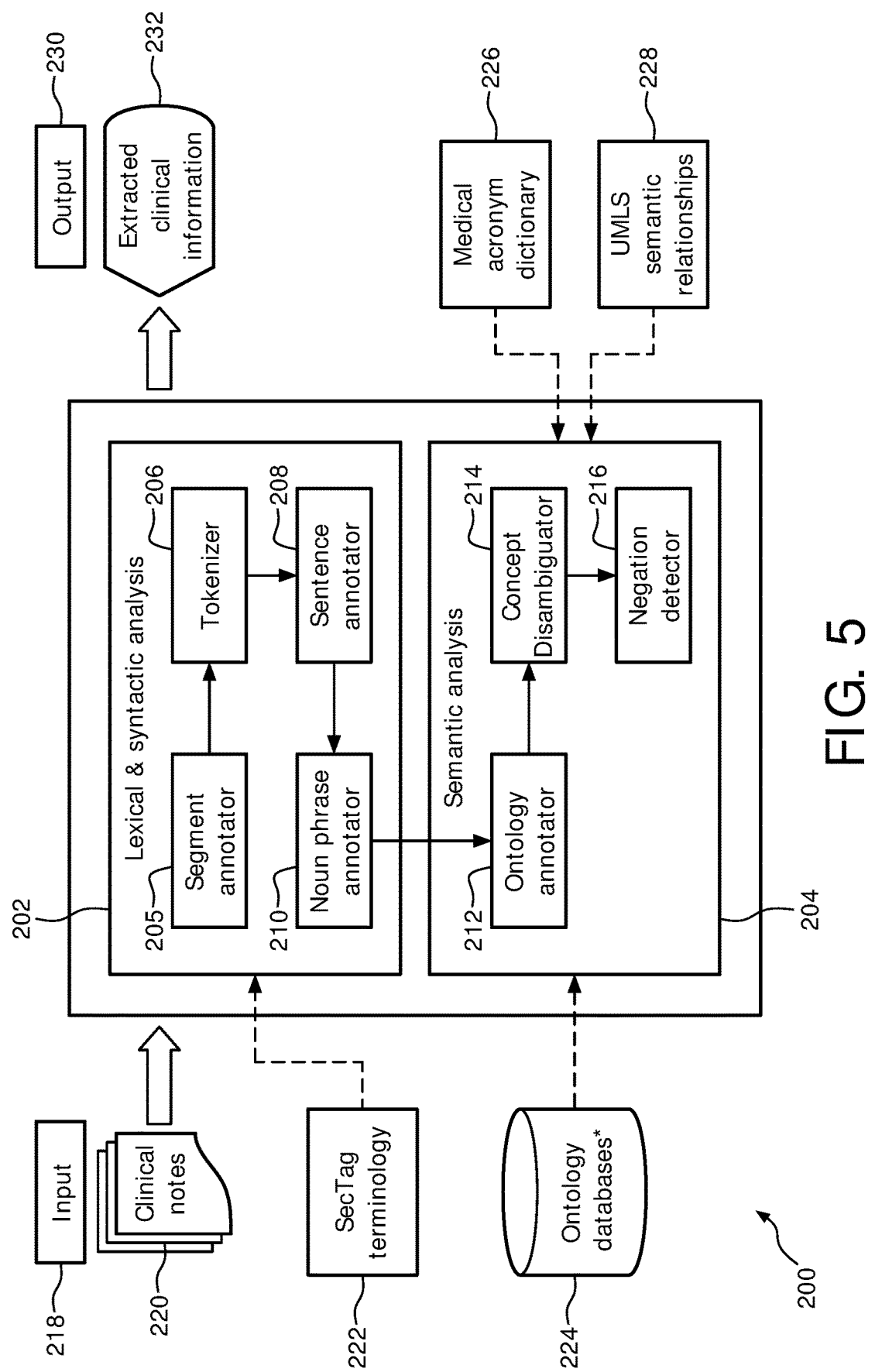
FIG. 5 illustrates a system for extracting active diagnoses from clinical documents, in accordance with one or more features described herein.

FIG. 5 illustrates a system 200 for extracting active diagnoses from clinical documents, in accordance with one or more features described herein. The system 200 comprises a lexical and syntactic analysis module 202 and a semantic analysis module 204. The lexical and syntactic analysis module 202 comprises a segment annotator module 205, a tokenizer module 206, a sentence annotator module 208, and a noun phrase annotator 210. The semantic analysis module comprises an ontology annotator 212, a concept disambiguator module 214, and a negation detector module 216. These modules act in concert on input 218 such as clinical documents or notes 220 to extract diagnoses from the clinical documents via a multi-step annotation process.

Document section header identification is performed by the segment annotator module 205 to identify specific sections of the clinical document that tend to have information related the patient's diagnoses. Such sections include without limitation: problem list, past medical history, history of present illness, etc. The headers for these sections are identified while the paragraphs/sentences under each section are indexed for further analysis.

The noun phrase annotator 210 performs noun phrase (NP) identification, wherein sentences within the clinical document are tagged with corresponding parts-of-speech (POS) and analyzed syntactically to identify NPs. These NPs represent concepts that are most likely (i.e., above a predetermined likelihood threshold) diagnoses or clinical findings.

The concept disambiguator module 214 performs Code Mapping Disambiguation, whereby diagnoses within the clinical document are mapped to related terms within SNOMED CT (Systematized Nomenclature of Medicine— Clinical terms), a comprehensive and widely used healthcare terminology. Subsequently, the candidate terms are disambiguated based on some heuristic rules in other to get the best result.

The negation detector module 216 performs negation detection whereby, based on sentence-level contextual information, it is determined if a diagnosis is negated and therefore should be excluded from the active diagnoses. For instance, in the phrase 'no evidence of pneumonia', 'pneumonia' is a diagnosis that is negated by the statement "no evidence of".

As outlined in FIG. 5, the starting point for an active diagnoses extraction algorithm is a free-text clinical document (e.g., a .xml. or .txt file, or the like) that is uploaded and analyzed by the segment annotator module 205. The knowledge source for the segment annotator module is, for instance, a SecTag terminology database 222, which is a database of over 6000 clinical document section headers. Sentences found under the relevant section headers are the inputs for, e.g., a probabilistic grammar parser (not shown), which assigns the POS tags and identifies NP terminals within each sentence. "NP terminal" denotes a NP that does not contain another NP; e.g. "acute coronary syndrome" is considered a NP terminal if each word in the concept is not a stand-alone NP.

Each NP terminal is used to generate dual keys that query the SNOMED CT database. A dual key is generated by concatenating the first 3 characters in a pair of words found within the NP terminal. For instance, if 'acute coronary syndrome' is a NP terminal, the dual keys comprising the concatenated characters "ACUCOR, ACUSYN and CORSYN" are be used to query the SNOMED CT database to retrieve the appropriate candidate terms. To select the most appropriate concept from the set of candidate SNOMED CT terms, the following rules are applied.

Hierarchical relevance: terms describing active diagnoses or concepts in specific hierarchies representing diagnostic information are selected in a particular order. The hierarchical order is as follows: Disorder>>Finding>>Morphologic Abnormality>>Body Structure>>Qualifier Value. For instance, "acute coronary syndrome" (disorder) is preferred to "acute post-thoracotomy pain syndrome" (finding) even if both terms occur in the same candidate set when the dual key 'ACUSYN' is used to query the SNOMED CT database.

Semantic similarity: the SNOMED CT tree (FIG. 7) representing the relationships associated with each term is compared to that of the concept within the NP terminal to evaluate their semantic relatedness. A term and the NP terminal concept are said to be semantically similar if they have the same nodes at the first five levels of the tree (or all levels if the tree is less than five levels deep). The threshold of five levels ensures that expected differences at deeper levels in the tree are less emphasized while evaluating semantic relatedness.

String matching using edit distance: by computing the differences in individual characters between the NP terminal concept and the corresponding SNOMED CT term, misspellings and typographical errors are accounted for during code mapping. For instance, "acute coronry syndrome" will be coded correctly as "acute coronary syndrome" in SNOMED CT.

When performing semantic analysis, several resources can be queried to assist in the analysis. For instance, one or more ontology databases 224 can be queried by the ontology annotator 212 to facilitate ontology annotation. Additionally, a medical acronym dictionary 226 and/or a UMLS semantic relationship database 228 can be queried by the concept disambiguator module 214 when resolving ambiguity among concepts. It will be appreciated that the system 200 can also comprise a processor and memory (not shown in FIG. 5) such as the processor 30 and memory 32 (FIG. 1) to perform the various functions and the like described herein.

Figure 6:
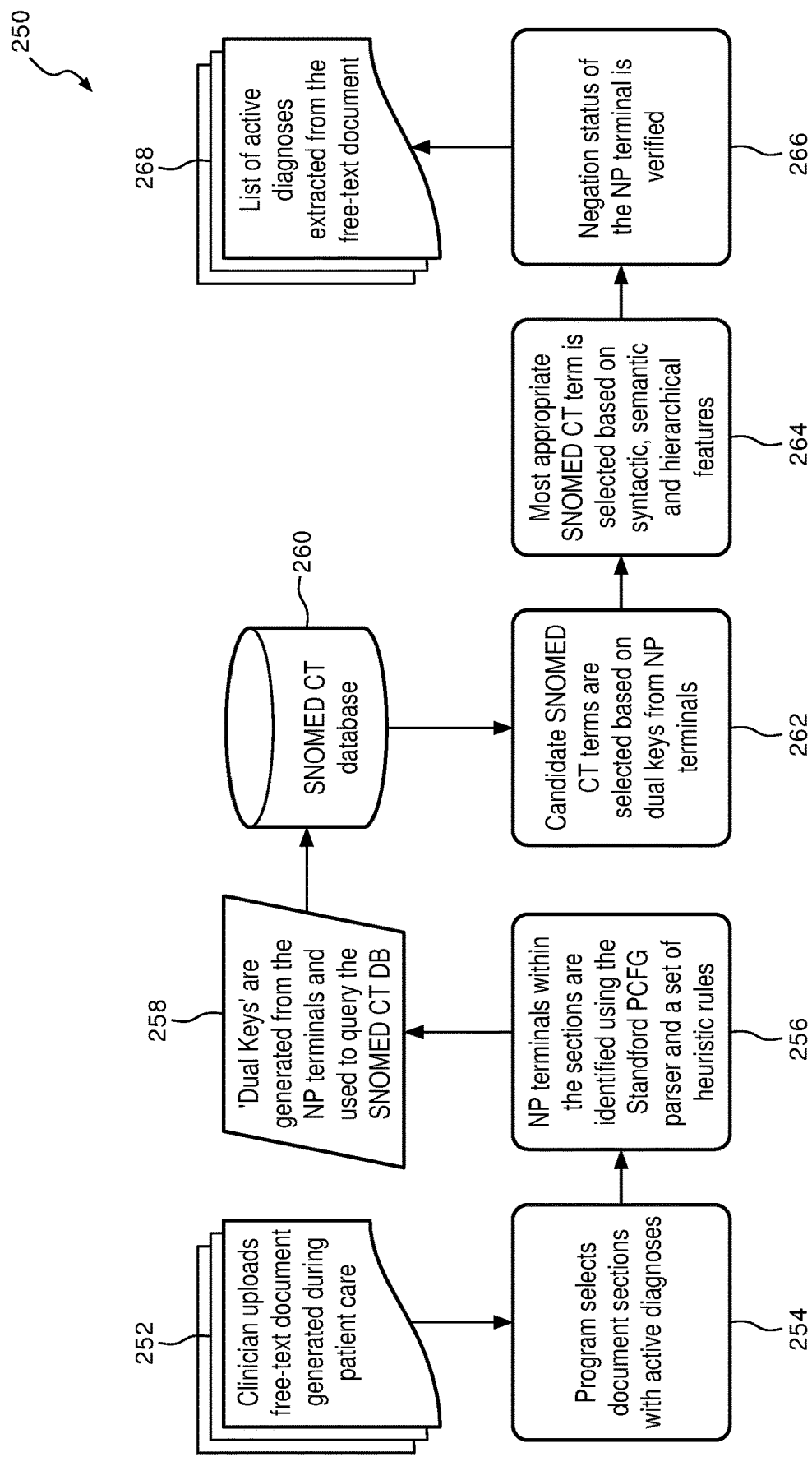
FIG. 6 shows a process flow extracting active diagnoses from clinical documents, in accordance with one or more features described herein.

FIG. 6 shows a process flow 250 extracting active diagnoses from clinical documents, in accordance with one or more features described herein. At 252, a clinician uploads a free-text document generated during patient care. At 254, document sections with active diagnoses are selected. At 256, NP terminals within the sections are identified using a parser and set of heuristic rules. At 258, dual keys are generated from the NP terminals and used to query a database 260, such as a SNOMED CT database. At 262, candidate SNOMED CT terms are selected based on the dual keys generated from the NP terminals. At 264, a most appropriate SNOMED CT term is selected based on syntactic, semantic, and hierarchical features. At 266, negation status of the NP terminal is verified. At 268, a list of active diagnoses is extracted from the free-text document.

FIG. 7 shows a SNOMED CT tree 270 for acute coronary syndrome such as is displayed to a clinician, in accordance with one or more features described herein. The tree 270 represents the relationships associated with each term is compared to that of the concept within the NP terminal to evaluate their semantic relatedness.

FIGS. 8-12 relate to the user interface or browser 12 of FIG. 1.

Figure 8:
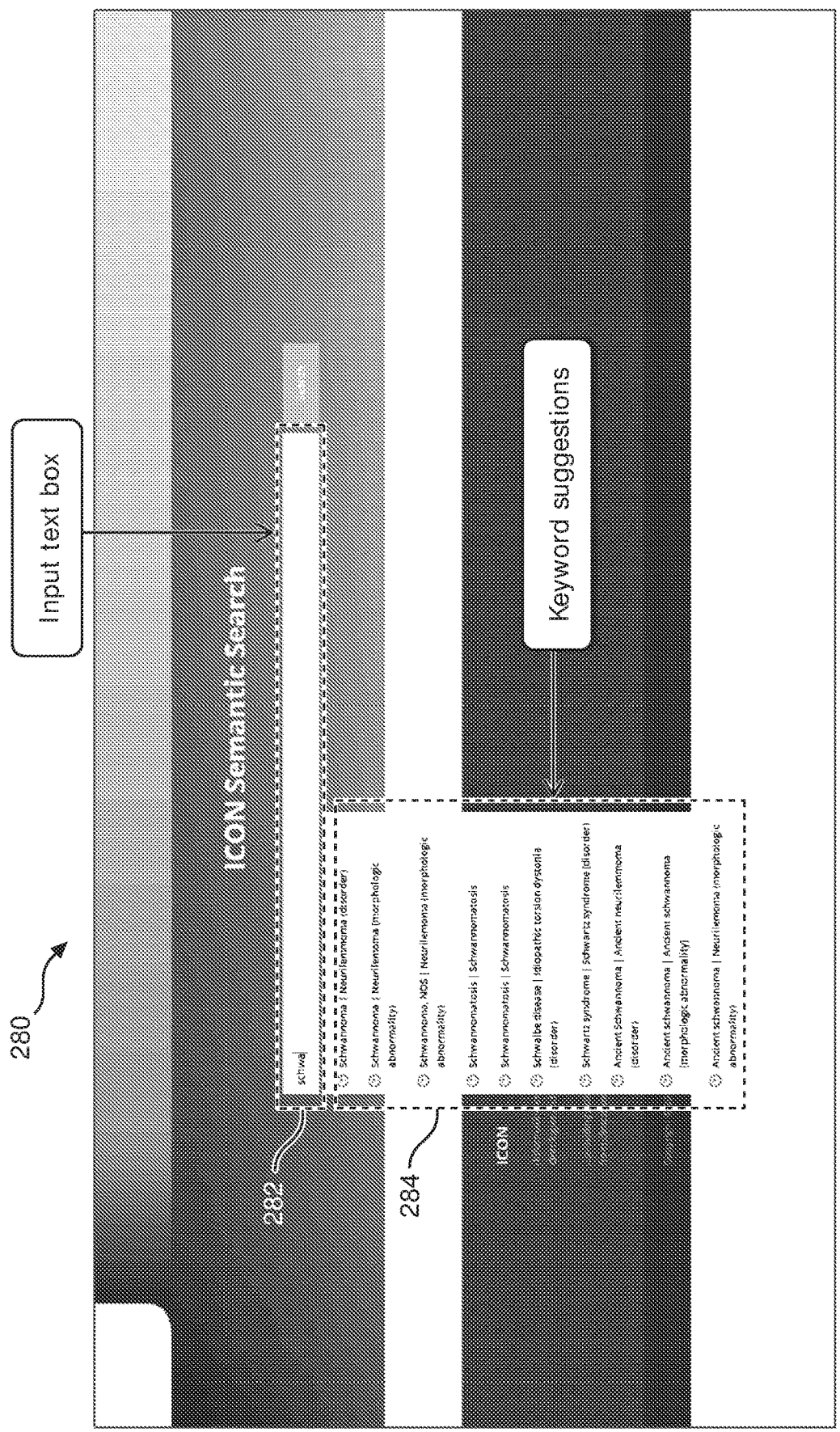
FIG. 8 is a screenshot of the user interface showing an input text box wherein a user can enter a keyword.

FIG. 8 is a screenshot 280 of the user interface showing an input text box 282 wherein a user can enter a keyword. As the user types, keyword suggestions 284 are presented to the user for selection. The ICON Semantic Search web-based framework is built on the Django web application framework which was modified to seamlessly transact with a NoSQL database (e.g., MongoDB™) to identify and present semantically-related clinical concepts driven by user-defined key word queries. The user enters a keyword in the input text box. On entering the key word(s), several related options representing synonyms and variants as derived from clinical knowledge sources are displayed to the user for possible selection. Thus, the user can select the most appropriate option from the drop-down suggestions related to the first few characters typed into the input text box.

By clicking the search button or selecting an option from the drop-down suggestions, the user sends the key word to the ICON Semantic Search engine for analysis and subsequent retrieval of contextual patient information representing semantically-related clinical concepts contained in a database of clinical reports. These reports would have been pre-processed by the ICON Semantic Search engine. In the example in FIG. 8, the user intends to type the key word 'Schwannoma' - a benign tumor of the outer covering of peripheral nerves in the human body. Suggestions are displayed from the clinical knowledge sources in the ICON Semantic Search engine linked to the web-based interface as triggered by the entry of the first few characters of the key word i.e. 'schwa'.

Subsequently, sections and sub-sections are displayed in the results panel highlighting both the key word (schwannoma) and other semantically-related concepts identified within the corresponding segments in multiple clinical reports belonging to an individual patient or patient population.

Figure 9:
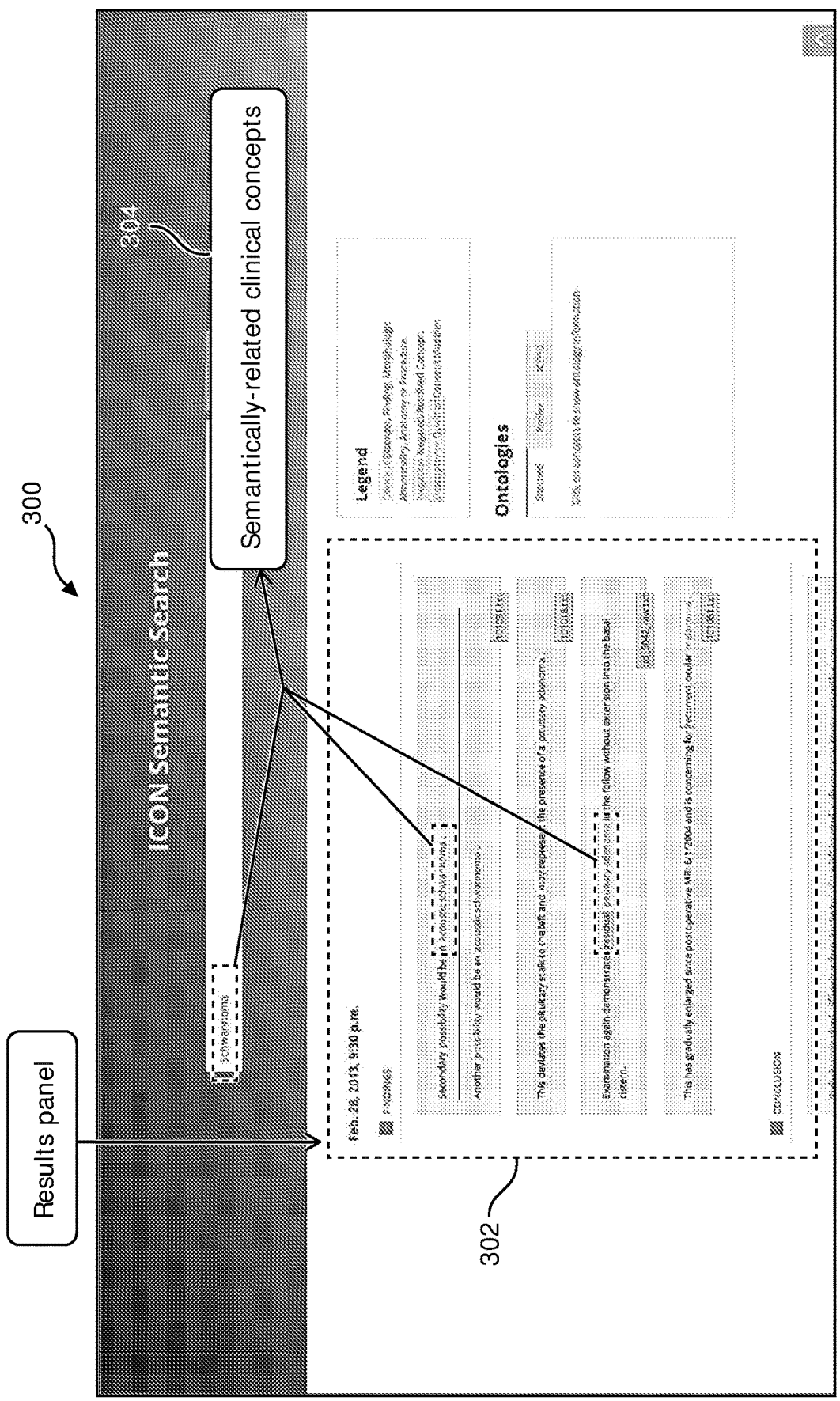
FIG. 9 is a screenshot of the web-based user interface showing search results highlighting semantically-related clinical concepts, in accordance with various aspects described herein.

FIG. 9 is a screenshot 300 of the web-based user interface showing search results highlighting semantically-related clinical concepts, in accordance with various aspects described herein. The interface includes a results panel 302 that displays context in the clinical report sections and sub-sections and highlights annotated clinical concepts 304 within the report that are semantically related to the keyword(s). For example, the concepts 'acoustic neuroma' (a specific type of schwannoma that develops on the nerve that connects the ear to the brain) and pituitary adenoma (common benign tumor of the pituitary gland located in the brain) are highlighted within different sections in different clinical reports. The three concepts (schwannoma, acoustic neuroma and pituitary adenoma) are semantically-related given they are all benign tumors that affect structures related to the brain. Thus, the ICON Semantic Search web-based interface offers the user actionable knowledge on the presence of these semantically-related concepts, potentially informing further investigations by the user on the quality of clinical management administered to address these conditions and the final outcomes.

Figure 10:
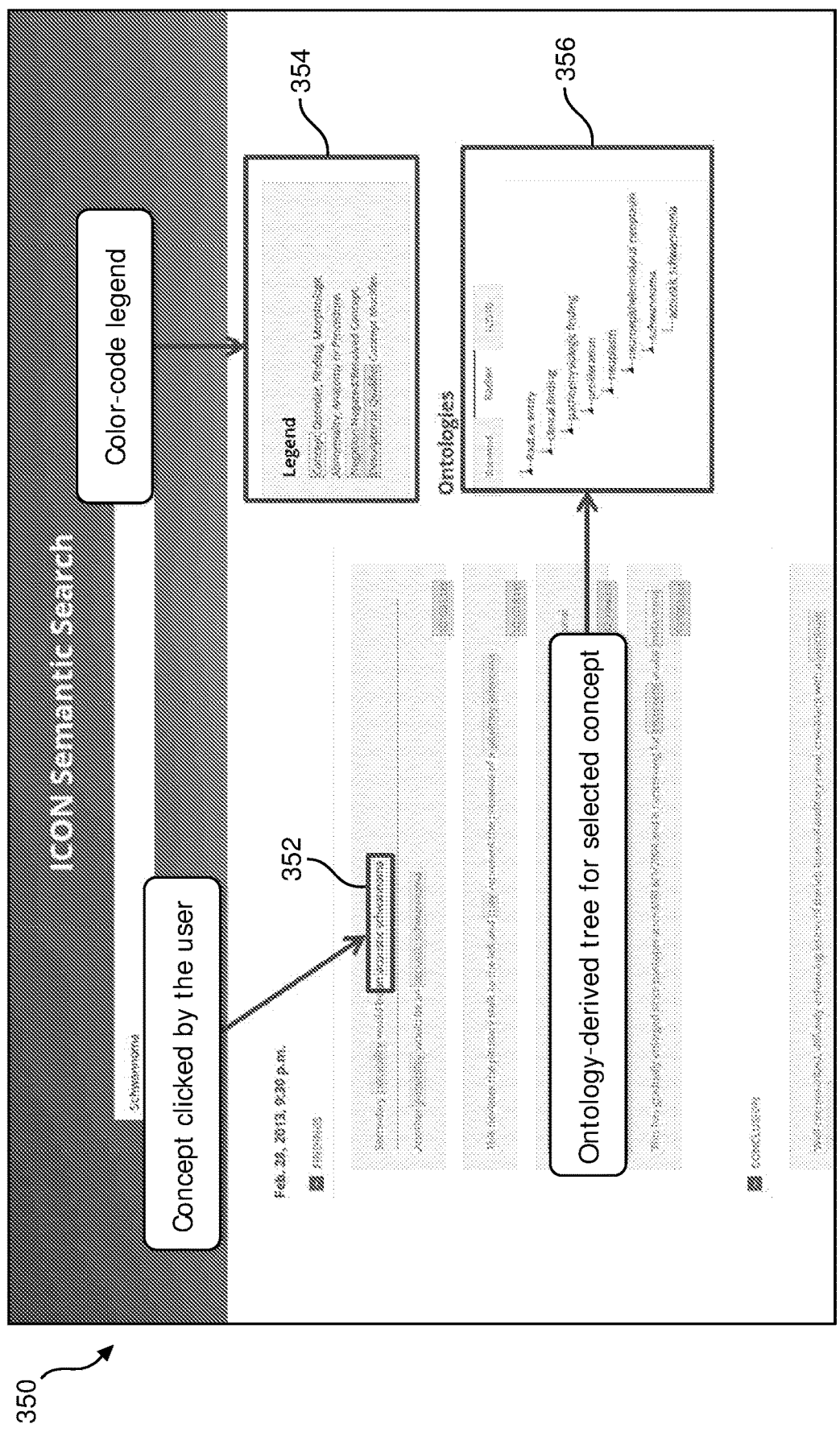
FIG. 10 is a screenshot of the web-based user interface showing a user-selected clinical concept, a color coded legend, and an ontology panel showing an ontology-derived tree for the user-selected concept.

FIG. 10 is a screenshot 350 of the web-based user interface showing a user-selected clinical concept, a color coded legend 354, and an ontology panel 356 showing an ontology-derived tree for the user-selected concept. The ontology panel presents the ontology-derived semantic tree related to annotated concepts within the display clinical reports. In addition to the semantic relationships, the interface displays the modifiers that are associated with the identified clinical concepts as well as the negation status of the semantically-related concepts. The modifiers and negation status, distinguished using the legend provided in the web-based interface color-coded legend 354, provide further contextual details that support the users' synthesis and comprehension of the clinical scenarios represented in the reports related to the key word search. On clicking a highlighted clinical concept, the ontology panel 356 displays the ontology-derived tree related to the concept, thus providing additional information on the parent-child relationships that define the highlighted concept.

Figure 11:
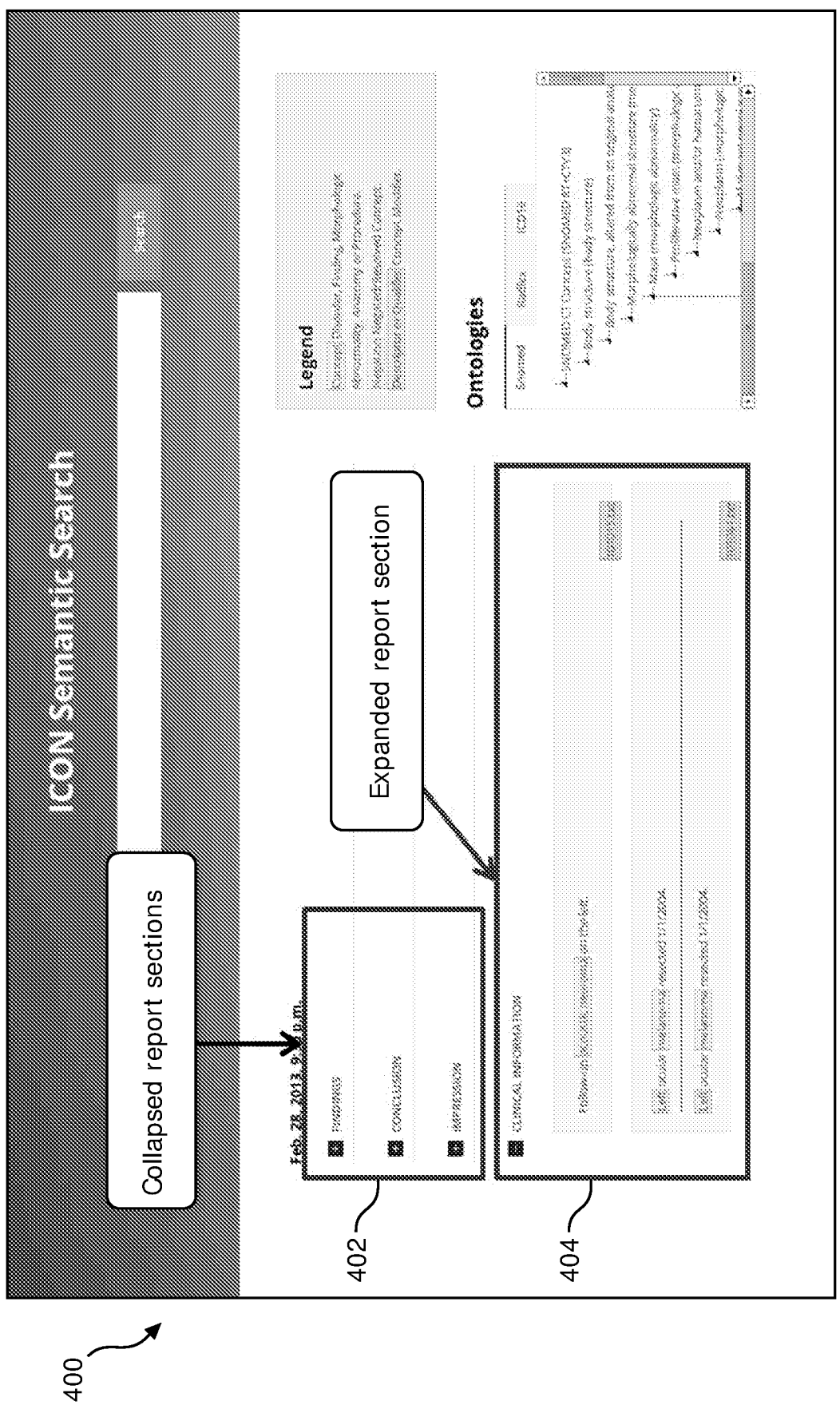
FIG. 11 is a screenshot of the web-based user interface showing collapsed report sections and an expanded report section.

FIG. 11 is a screenshot 400 of the web-based user interface showing collapsed report sections 402 and an expanded report section 404. The expanded report section 404 provides access to the complete clinical context for further review of the semantic relationships highlighted in the web-based interface, e.g., via a hyperlink that displays the full text in a selected clinical report. This aspect of the interface enhances the users' navigation through the clinical reports by allowing the collapse/expansion of the sections and sub-sections containing the semantically-related clinical concepts.

Figure 12:
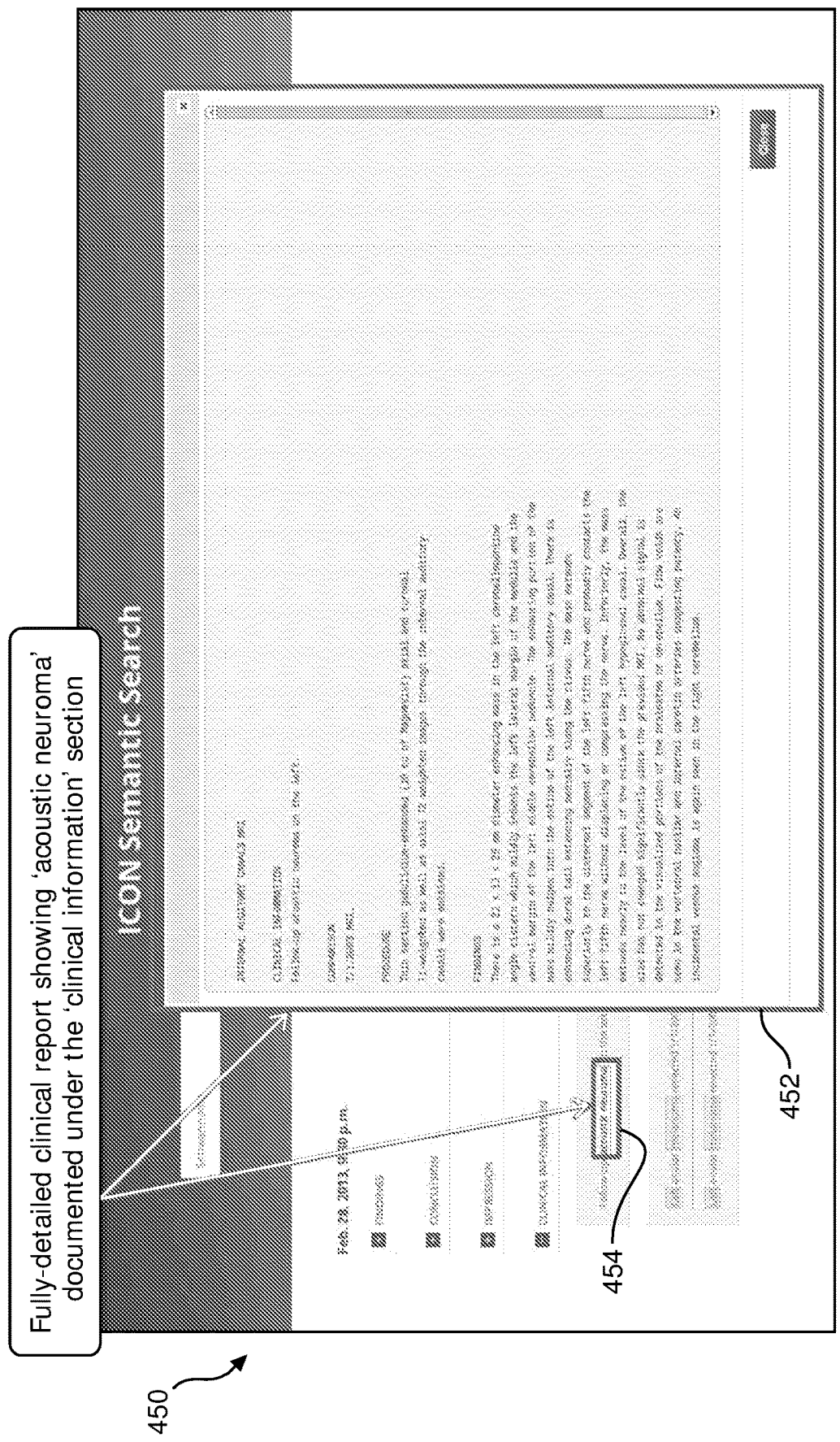
FIG. 12 shows a screenshot of the web-based user interface in which a full clinical report is displayed with the highlighted clinical concept.

FIG. 12 shows a screenshot 450 of the web-based user interface in which a full clinical report 452 is displayed with the highlighted clinical concept 454. This feature of the web-based interface allows users to have access to the complete clinical report text via a button adjacent to the corresponding snippet of contextual clinical information derived from the report. On clicking this hyperlink button, the free text documentation is displayed in a separate window, allowing the user to further review and confirm his/her hypotheses derived from the semantically-related concepts captured across various clinical reports. In the example in FIG. 12, the user clicked on the corresponding full clinical report that had the statement "follow-up acoustic neuroma on the left" entered under the "clinical information" section. By reviewing the full text, the user can review and verify whether the findings at follow-up revealed improvement or worsening of the acoustic neuroma. The ICON Semantic Search engine web-based interface thus provides actionable knowledge based on semantically-related clinically concepts directed towards informing optimal evaluation of healthcare management and quality via synthesis of clinical reports at the individual-patient and population levels.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system that facilitates using user-entered keywords to search for related clinical concepts based on the semantic meaning of the keywords, comprising:
   a client web interface configured to receive keyword search information and display at least one expandable and collapsible report section associated with a document section identified based on at least one terminology knowledge source;
   a web server configured to communicate with the client web interface;
   a semantic analysis engine configured to:
      receive the keyword search information via the web server,
      analyze the received keyword search information,
      map the analyzed received keyword search information to at least one Unified Medical Language System (UMLS) concept;
      identify and retrieve, from the at least one mapped UMLS concept, one or more related concepts based on one or more relational knowledge sources, and
      transmit the one or more related concepts to the web server; and
   a natural language processing (NLP) engine configured to communicate with the semantic analysis engine via a structured query language database, wherein the NLP engine is configured to receive and store free-text clinical notes and information, extract clinical concepts from the clinical notes and information, and store the clinical concepts into a NoSQL database, wherein the clinical concepts comprise at least one diagnosis, finding, or procedure;
   wherein the web server uses the one or more related concepts transmitted by the semantic analysis engine to query the NoSQL database to find relevant clinical notes that include the one or more related concepts and the web server returns a list of relevant clinical notes that includes the one or more related concepts for display to a user via the client web interface, and
   wherein when the at least one expandable and collapsible report section is expanded, the client web interface comprises:
      a list of contextual information for at least two of the relevant clinical notes, each of the at least two of the relevant clinical notes including the one or more related concepts that are highlighted and selectable by a user, wherein each of the one or more related concepts is semantically related to the keyword search information; and
      a selectable link to the user to a full clinical report associated with the user selectable one or more related concepts for each of the at least two relevant clinical notes.

2. The system according to claim 1, wherein the web server is further configured to present the list of relevant clinical notes that includes the one or more related concepts via the client web interface as a list of clinical notes with relevant concepts highlighted for user selection.

3. The system according to claim 2, wherein, upon receiving input related to a user selection of a highlighted concept, the web server displays via the client web interface a tree structure of the selected concept within one or more ontologies.

4. The system according to claim 3, wherein the web server is further configured to present original notes comprising the selected concept via the client web interface.

5. The system according to claim 1, wherein the list is arranged in chronological order of the creation of the notes comprising the relevant concepts.

6. The system according to claim 1, wherein the semantic analysis engine comprises a spell checker module configured to detect and correct spelling errors in the keyword search information and map one or more keywords to one or more clinical concepts.

7. The system according to claim 6, wherein the spell checker module maps the one or more keywords to the one or more clinical concepts by executing a fuzzy string matching algorithm.

8. The system according to claim 1, wherein the semantic analysis engine further comprises a relationship discovery module configured to identify the one or more related concepts related to the UMLS concept.

9. A method of facilitating using user-entered keywords to search for related clinical concepts based on the semantic meaning of the keywords, comprising:
   receiving, by a natural language processing (NLP) engine, a free-text electronic document generated during patient care;
   identifying, by a segment annotator module of the NLP engine, document sections with active diagnoses in the free-text electronic document based on at least one terminology knowledge source;
   indexing at least one sentence within the identified document sections;
   inputting the at least one sentence within the identified document sections and identifying, by a noun phrase annotator of the NLP engine, at least one noun-phrase (NP) terminal within the at least one sentence, where the at least one NP terminal comprises at least two words and each word is not a noun phrase on its own and the at least one NP terminal comprises a concept comprising a diagnostic or clinical finding based on an exceeded predetermined likelihood threshold;
   generating dual keys from the at least one NP terminal;
   querying a database using the dual keys to retrieve candidate active diagnoses;
   selecting a candidate active diagnosis that is most-similar to the at least one NP terminal based on syntactic, semantic, and hierarchical features;
   extracting a list of active diagnoses from the free-text electronic document; analyzing a hierarchical tree that represents relationships associated with words within each candidate active diagnosis as compared to that of words within the concept identified within the at least one NP terminal to evaluate a semantic relatedness between the given active diagnosis and the NP terminal concept; and displaying, via a results panel on a graphical user interface, at least one expandable and collapsible report section associated with at least one of the identified document sections, wherein the at least one expandable and collapsible report section comprises when expanded:

contextual information for the free-text electronic document a selectable highlighted annotated word within the extracted active diagnosis within the contextual information; and a selectable link to the user to a full version of the free-text electronic document associated with the user selected word within the extracted active diagnosis.

10. The method according to claim 9, further comprising identifying the at least one NP terminal within the identified document sections using a probabilistic parser and set of heuristic rules.

11. The method according to claim 9, wherein the database is a SNOMED CT database.

12. The method according to claim 9, further comprising verifying a negation status of the at least one NP terminal, such that if the negation status is negated by one or more words associated with the at least one NP terminal, then the active diagnosis associated with the at least one NP terminal is excluded from the list.

13. The method according to claim 9, wherein the dual keys are generated by concatenating the first 3 characters in a pair of words found within a given NP terminal.

14. The method according to claim 9, wherein the candidate active diagnosis and a NP terminal concept are semantically similar if they have the same nodes at a first five levels of the tree, or at all levels if the tree is less than five levels deep.

15. The method according to claim 9, wherein the selected candidate active diagnosis and a NP terminal concept are semantically most-similar when the selected candidate active diagnosis has more common nodes in the tree than other candidate active diagnoses.

16. A graphical user interface that facilitates presenting clinical concepts related to user- entered keywords based on the semantic meaning of the keywords, comprising:

a keyword field via which a user enters or selects one or more keywords;

an ontology panel configured to display an ontology derived tree for a user selected clinical concept; and a results panel configured to display at least one expandable and collapsible report section associated with a document section identified based on at least one terminology knowledge source, the at least one expandable and collapsible report section comprising when expanded:

a list of contextual information for at least two clinical reports;

a selectable highlighted annotated clinical concept within the listed contextual information for each of the at least two clinical reports, wherein each of the highlighted annotated clinical concepts is semantically related to the one or more keywords; and a selectable link for each of the at least two clinical reports to the user to a full clinical report associated with the user selected clinical concept.

17. The graphical user interface of claim 16, wherein upon receiving input related to a user selection of the highlighted annotated clinical concept, the graphical user interface displays the ontology-derived tree of the selected highlighted annotated clinical concept within one or more ontologies.

18. The graphical user interface of claim 16, wherein the graphical user interface is configured to present the full clinical report comprising the selected highlighted annotated clinical concept for each of the at least two clinical reports.

19. The graphical user interface of claim 18, wherein the full clinical reports are arranged in chronological order based on the creation of the reports.

* * * * *